(12) United States Patent
Scheidel et al.

(10) Patent No.: US 7,566,800 B2
(45) Date of Patent: Jul. 28, 2009

(54) HOMOGENEOUS ISOMERIZATION OF CIS-2-PENTENE NITRILE TO FORM 3-PENTENE NITRILE

(75) Inventors: Jens Scheidel, Hirschberg (DE); Christian Miller, Ruppertsberg (DE); Robert Baumann, Mannheim (DE); Tim Jungkamp, Kapellen (BE); Michael Bartsch, Neustadt (DE); Gerd Haderlein, Grünstadt (DE); Hermann Luyken, Ludwigshafen (DE); Wolfgang Siegel, Limburgerhof (DE); Peter Bassler, Viernheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 567 days.

(21) Appl. No.: 10/586,481

(22) PCT Filed: Jan. 27, 2005

(86) PCT No.: PCT/EP2005/000770

§ 371 (c)(1),
(2), (4) Date: Jul. 20, 2006

(87) PCT Pub. No.: WO2005/073176

PCT Pub. Date: Aug. 11, 2005

(65) Prior Publication Data

US 2007/0155980 A1 Jul. 5, 2007

(30) Foreign Application Priority Data

Jan. 29, 2004 (DE) .................. 10 2004 004 717

(51) Int. Cl.
*C07D 291/00* (2006.01)
(52) U.S. Cl. ...................... 558/355
(58) Field of Classification Search ...................... None
See application file for complete search history.

(56) References Cited

U.S. PATENT DOCUMENTS 3,526,654 A 9/1970 Hildebrand
3,564,040 A 2/1971 Downing et al.
3,852,325 A 12/1974 King

FOREIGN PATENT DOCUMENTS

DE 103 23 803 11/2004
EP 1 191 018 A1 3/2002

OTHER PUBLICATIONS

W. von E. Doering et al. "CryptoCope Rearrangement of 1,3-Dicyano-5-phenyl-4,4-$d_2$-hexa-2,5-diene. Chameleonic or Centauric?" *J. Am. Chem. Soc.* 1999, 121, 10967-10975.

*Primary Examiner*—Kamal A Saeed
(74) *Attorney, Agent, or Firm*—Connolly Bove Lodge & Hutz LLP

(57) ABSTRACT

The invention relates to a method for isomerization of pentene nitrile in an educt flow, wherein isomerization is performed on a homogeneously dissolved catalyst.

8 Claims, No Drawings

HOMOGENEOUS ISOMERIZATION OF CIS-2-PENTENE NITRILE TO FORM 3-PENTENE NITRILE

CROSS REFERENCE TO RELATED APPLICATIONS

This application is a National Phase of PCT/EP2005/000770, filed Jan. 27, 2005, which claims priority to German application 10 2004 004 717.0 filed Jan. 29, 2004.

The present invention relates to a process for isomerizing pentenenitrile in a reactant stream.

Adiponitrile is an important starting material in nylon production and is obtained by double hydrocyanation of 1,3-butadiene. In the first hydrocyanation, the 1,3-butadiene is hydrocyanated to 3-pentenenitrile, in the course of which the by-products obtained are mainly cis-2-pentenenitrile, 2-methyl-3-butenenitrile, 2-methyl-2-butenenitrile, $C_9$ nitriles and methylglutaronitrile. In a second, subsequent hydrocyanation, 3-pentenenitrile is reacted with hydrogen cyanide to give adiponitrile. Both hydrocyanations are catalyzed by nickel (0)-phosphorus complexes. Unlike 3-pentenenitrile, for example trans-3-pentenenitrile, the cis-2-pentenenitrile cannot be hydrocyanated to adiponitrile in the presence of nickel (0)-containing catalysts. This reduces the yield of the adiponitrile synthesis.

It is accordingly desirable to isomerize cis-2-pentenenitrile to trans-3-pentenenitrile, in order then to be able to recycle it back into the adiponitrile synthesis.

U.S. Pat. No. 3,526,654 discloses the isomerization of cis-2-pentenenitrile to trans-3-pentenenitrile in the presence of silicon dioxide, alumina or sodium-calcium silicate, the catalysts being present in various modifications. The isomerization is carried out in the liquid or gas phase at temperatures of from 25° C. to 500° C. Owing to a low conversion and a long isomerization time, this process is uneconomic. In general, the rate of an isomerization can be raised by an increase in the reaction temperature. However, this is not appropriate to the purpose in the present isomerization of cis-2-pentenenitrile to trans-3-pentenenitrile, since, in the case of pentenenitriles, an increase in the reaction temperature within the temperature range disclosed in U.S. Pat. No. 3,526,654 leads to formation of an industrially unacceptable high amount of oligomers and polymers.

DE-A-103 23 803 describes the isomerization of cis-2-pentenenitrile to 3-pentenenitrile over alumina as a catalyst. In this isomerization, yields of 30% based on cis-2-pentenenitrile are generally achieved. When the conversion of cis-2-pentenenitrile is increased, the result is increased formation of trans-2-pentenenitrile relative to the desired formation of trans-3-pentenenitrile.

It is thus an object of the present invention to provide a process which enables the isomerization, especially of cis-2-pentenenitrile to trans-3-pentenenitrile, with conversions based on the isomerization reactant which are economically acceptable. At the same time, a high space-time yield of trans-3-pentenenitrile based on cis-2-pentenenitrile should be achieved.

The object of the present invention is achieved by a process for isomerizing pentenenitriles in a reactant stream.

In the process according to the invention, the isomerization takes place over at least one homogeneously dissolved catalyst.

In a preferred embodiment of the present invention, cis-2-pentenenitril is isomerized to trans-3-pentenenitrile.

In an isomerization of cis-2-pentenenitrile, the reactant stream may comprise further constituents which are in particular selected from the group consisting of C5-mononitriles, C6-dinitriles, aliphatic C1- to C16-alkanes, cyclic C1- to C16-alkanes, aliphatic C1- to C16-alkenes, cyclic C1- to C16-alkenes, more preferably starting from a group consisting of trans-3-pentenenitrile, trans-2-pentenenitrile, cis-3-pentenenitrile, 4-pentenenitrile, Z-2-methyl-2-butenenitrile, E-2-methyl-2-butenenitrile, 2-methyl-3-butenenitrile, methylglutaronitrile, ethylsuccinonitrile, adiponitrile, valeronitrile, cyclohexane, methylcyclohexane, n-heptane, n-octane, vinylcyclohexane, ethylidenecyclohexene and vinylcyclohexene.

The content of cis-2-pentenenitrile in the reactant stream is preferably from 0.5 to 100% by weight, more preferably from 1.0 to 98% by weight, in particular from 1.5 to 97% by weight.

The reactant stream used in the process according to the invention, which comprises cis-2-pentenenitrile, is generally obtained in processes known per se. An example thereof is a process for hydrocyanating 3-pentenenitrile, 3-pentenenitrile referring to trans-3-pentenenitrile, cis-3-pentenenitrile, mixtures thereof or a mixture comprising cis- or trans-3-pentenenitrile. Alternatively, the reactant stream may also stem from a hydrocyanation of 4-pentenenitrile or mixtures comprising 4-pentenenitrile to adiponitrile.

In a preferred embodiment, the process according to the invention may be integrated into a hydrocyanation process for preparing adiponitrile.

EMBODIMENT I

In a first preferred embodiment, the inventive isomerization may be carried out in any suitable apparatus known to those skilled in the art. Suitable apparatus for the reaction is thus customary apparatus, as described, for example, in: Kirk-Othmer, Encyclopedia of Chemical Technology, 4th Ed., Vol. 20, John Wiley & Sons, New York, 1996, pages 1040 to 1055, such as stirred tank reactors, loop reactors, gas circulation reactors, bubble column reactors or tubular reactors, preferably tubular reactors, in each case if appropriate with apparatus for heat transfer. The reaction may be carried out in a plurality of, such as two or three, apparatuses.

After the reaction, the reaction effluent is preferably worked up distillatively.

This distillation may be carried out in any suitable apparatus known to those skilled in the art. Suitable apparatus for distillation is as described, for example, in: Kirk-Othmer, Encyclopedia of Chemical Technology, 4th Ed., Vol. 8, John Wiley & Sons, New York, 1996, pages 334 to 338, such as sieve tray columns, bubble-cap tray columns, columns having structured packing or random packing, which may also be operated as dividing wall columns. These distillation apparatuses are each equipped with suitable apparatus for evaporation, such as falling-film evaporators, thin-film evaporators, multiphase helical tubular evaporators, natural circulation evaporators or forced circulation flash evaporators, and also with apparatus for condensing the vapor stream. The distillation may be carried out in a plurality of, such as two or three, apparatuses. The distillation may additionally be effected in one stage in the case of a partial evaporation of the feed stream.

In this distillation, a stream enriched in isomerization product, preferably 3-pentenenitrile, compared to the reaction effluent is obtained in the bottom, and a stream depleted in isomerization product, preferably 3-pentenenitrile, compared to the reaction effluent is obtained as the top stream. The bottom stream may preferably be fed to a process for hydrocyanating 3-pentenenitrile, in which case remaining homogeneously dissolved catalyst is, if appropriate, removed beforehand in a suitable manner, preferably by distillation.

Accordingly, the process of embodiment I is carried out preferably in an apparatus unit comprising at least one reactor and at least one distillation apparatus, the reactors, if more than one reactor is used, being connected directly in series, and the distillation apparatuses, if more than one distillation apparatus is used, being connected directly in series, and the at least one distillation apparatus being connected downstream of the at least one reactor.

In the context of the present invention, "connected directly downstream" and "the at least one distillation apparatus being connected directly downstream of the at least one reactor" mean that the reactors are connected in series without interruption by distillation apparatus, so that the isomerization stream is not conducted into the first distillation apparatus until it has passed through all reactors present.

EMBODIMENT II

One means of improving the conversion is to remove the reaction product of the isomerization, in order thus to shift the equilibrium to the side of the desired isomerized pentenenitrile. One means of removing the isomerized pentenenitrile from the equilibrium is to utilize the higher boiling point of the isomerized pentenenitrile in comparison to the pentenenitrile to be isomerized. From this arises initially a second preferred embodiment.

In this second preferred embodiment, at least two apparatus units according to embodiment I are connected in series in such a way that the top stream of the distillation apparatus which has been depleted in isomerization product, preferably 3-pentenenitrile, is used as the reactant stream of the apparatus unit, downstream in the battery, according to embodiment I. The bottom streams may be freed, preferably distillatively, separately or together, if appropriate, of remaining homogeneously dissolved catalyst in a suitable manner, and subsequently, for example, fed to a process for hydrocyanating 3-penetenitrile. Particular preference is given to working up the bottom streams together and likewise removing cis-2-pentenenitrile which is yet to be converted and recycling it back into the battery as a reactant stream. The catalyst stream may be conducted fully into the reactor of the first apparatus units according to embodiment I, or divided and conducted in portions in each case into the reactors of the apparatus units connected in series according to embodiment I.

The process according to embodiment II is thus effected preferably in more than one apparatus unit, the individual apparatus units being connected in series and the individual apparatus units comprising at least one reactor and at least one distillation apparatus, the reactors of the individual apparatus units, if more than one reactor is used in the apparatus unit, being connected directly in series, and the distillation apparatuses of the individual apparatus units, if more than one distillation apparatus is used in the particular apparatus unit, being connected directly in series, and the at least one distillation apparatus being connected downstream of the at least one reactor in the particular apparatus unit.

In the embodiments I and II, the catalyst stream may consist of freshly used catalyst and any recycled catalyst which is obtained in the removal from the at least one bottom stream.

EMBODIMENT III

Embodiment III constitutes a further means of increasing the conversion by the removal of the reaction product of the isomerization from the equilibrium.

According to the third preferred embodiment, the process according to the invention may be carried out in a distillation column at least comprising a bottom zone, a reaction zone and a top zone. The bottom zone, reaction zone and top zone are arranged in the sequence given above from bottom to top in the distillation column. It is not ruled out that reaction may also take place in the bottom or top zone.

If the isomerization is carried out in an distillation column, the distillation column may additionally comprise internals having distillative separating action. These additional internals are preferably disposed above the reaction zone. In the upper separating zone, i.e. the separating zone above the reaction zone, low-boiling secondary components are removed substantially from high-boiling components. Here, for example, any E-2-methyl-2-butenenitrile introduced with the reactant stream is separated from trans-3-pentenenitrile and trans-2-pentenenitrile. Equally, trans-3-pentenenitrile and trans-2-pentenenitrile may be depleted from nonisomerized cis-2-pentenenitrile.

The separating action of the internals in the reaction zone removes the high-boiling isomerization product substantially from low-boiling components. For example, trans-2-pentenenitrile and trans-3-pentenenitrile are separated from unconverted cis-2-pentenenitrile.

These separations are only detailed by way of example and are not limiting.

The division of the column into a purely distillative separating zone and a reaction zone is determined by the feed point of the medium comprising the catalyst and the evaporation behavior of the catalyst under the existing pressure and temperature conditions.

In the event of optimal column configuration, all of the cis-2-pentenenitrile of the reactant stream may be converted without additional reactor and all of the trans-3-pentenenitrile obtained in the bottom without an additional separating apparatus. The additional internals having distillative separating action (separating zone) are generally advantageous, but not necessarily required.

Separating zone and reaction zone of any distillation column used consist generally of a plurality of different subregions having different functions. The subregions differ by the task of transporting gas to the top of a column and the task of drawing liquid in the direction of the column bottom. In addition, liquid distributors may be necessary within the reaction zone, in order to ensure optimal distribution of liquid over the column cross section. Internals for introducing heat into the column may also be disposed in the reaction zone.

To achieve the distillative separating action of the distillation column, internals having distillative separating action are used. The internals used for the distillation columns are preferably structured sheet metal packings, structured fabric packings, bubble-cap trays, dual-flow trays or beds of random packings, or combinations of two or more of these classes of separating internals.

Preference is also given to using column internals having a high number of separation stages, such as metal fabric packings or sheet metal packings having ordered structure, for example Sulzer MELAPAK, Sulzer BX, Montz B1 types or Montz A3 types. To carry out the process according to the invention, preference is given to using distillation columns which, including the reaction and separating zones, have from 10 to 100 trays, more preferably from 10 to 60 trays. The same applies to what are known as theoretical plates in the case of other column internals.

The dimension of the reaction zone of the distillation column depends upon the desired degree of conversion and the amount of cis-2-pentenenitrile in the reactant stream. The feed of the medium comprising the catalyst is preferably 10, more preferably 5, theoretical distillation stages below the top draw, especially above the feed point at which the reflux is also conducted to the column.

The catalyst may be introduced to the column with, or separate from, the reactant stream.

The reactant stream or streams, referred to here only as the reactant stream, may be fed via various feed points of the column.

In the distillation column, pressure and temperature are preferably adjusted in such a way that high reaction rates are attained at sufficiently high selectivity. The pressure in the top zone is advantageously adjusted in such a way that the temperature in the bottom zone is between 30 and 300° C., preferably between 40 and 250° C., in particular between 50 and 200° C. The residence time in the distillation column is preferably from 1 minute to 10 hours, more preferably from 12 minutes to 3 hours.

The optimal temperature and pressure conditions are determined generally by the insertion of the isomerization into a process, for example with double hydrocyanation of 1,3-butadiene to adiponitrile, and the working temperature of the catalyst. The pressure may be adjusted using a vacuum pump and/or a pressure regulation device, so that the pressure conditions are matched to the demands of the process.

To increase the residence time in the reaction zone, it is possible to pass a substream through one or more side draws out of the distillation column through one or more vessels, and, if appropriate, to recycle the substreams leaving these vessels back into the column with the aid of a pump in each case. The vessels may be charged with heterogeneous catalyst. In a preferred embodiment, the vessels are heated. The temperature in the vessels should preferably correspond to the temperature of the liquid phase at the draw tray.

It has also been found to be advantageous when heat is supplied to the distillation system, consisting of the distillation column and, if appropriate, the vessel or the vessels, not only via the evaporator, but also additionally via external heat exchangers, or via heat exchangers disposed directly on the column internals.

It is additionally possible to draw off substreams via side draws from any points in the column. For example, it is also possible to operate the column under total reflux and discharge intermediate boilers within the boiling range between the pentenenitrile to be isomerized and the isomerized pentenenitrile via a side draw below the catalyst packing but above the feed.

If a distillation column is used in the process according to the invention, at the top of the column accumulates unconverted pentenenitrile to be isomerized and any components from the reactant stream which have a lower boiling point than the pentenenitrile to be isomerized, in some cases together with low-boiling by-products of the isomerization. In a preferred embodiment of the present invention, this top stream is conducted via a line into a condenser, condensed and discharged via a further line. A portion of the condensate may preferably be discharged back into the distillation column as reflux. In a preferred embodiment, the amount of the portion of the condensate which is introduced back to the column is more than 50% of the condensate, preferably more than 90% of the condensate. In this way, the internal reflux in the column allows an advantageous concentration profile to be attained.

The process according to the invention is carried out over a homogeneous catalyst which is preferably selected from the group of the C1- to C20-mono- and -diamines, preferably the C4- to C9-diamines, more preferably hexylamine. In addition, the homogeneous catalyst to be used may be an ionic liquid which is selected from the group consisting of Brønsted acid adducts of organic nitrogen-containing substances.

In a particularly preferred embodiment according to one of the embodiments I to III, the process according to the invention for isomerization may be integrated into an overall process, in which
  a) 3-pentenenitrile or a mixture comprising 3-pentenenitrile is hydrocyanated to adiponitrile in the presence of a nickel(0)-containing catalyst by processes known per se while obtaining cis-2-pentenenitrile as a by-product,
  b) cis-2-pentenenitrile is removed fully or partly from the product mixture, if appropriate together with other substances, from the hydrocyanation, for example by distillation,
  c) cis-2-pentenenitrile from step b) is isomerized by the above-described process according to the invention to obtain a bottom stream comprising trans-3-pentenenitrile, with or without further compounds which are selected from the group consisting of trans-2-pentenenitrile, 4-pentenenitrile and cis-3-pentenenitrile, and a top stream comprising nonisomerized cis-2-pentenenitrile and any compounds having a lower boiling point than trans-3-pentenenitrile and which are selected from the group consisting of C5-nitriles, for example Z-2-methyl-2-butenenitrile, E-2-methyl-2-butenenitrile, 2-methyl-3-butenenitrile, valeronitrile and other components stemming from the hydrocyanation and having a lower boiling point than trans-3-pentenenitrile,
  d) any cis-2-pentenenitrile present is removed from the bottom stream obtained in step c), for example by distillation, and recycled into step c) while obtaining a residual stream,
  e) the residual stream obtained in step d), if appropriate with suitable removal of any isomerization catalyst present, is recycled fully or partly into step a).

The bottom stream from c) may contain a residual proportion of cis-2-pentenenitrile. This proportion is preferably less than 10% by weight, more preferably less than 1% by weight, based on the bottom stream.

The top stream from c) may contain a residual proportion of trans-3-pentenenitrile. This proportion is preferably less than 10% by weight, more preferably less than 5% by weight, based on the top stream.

In step a), the nickel(0)-containing catalyst used may preferably be one which, in addition to nickel(0), also has a monovalent or a polyvalent ligand or a mixture of monovalent and polyvalent ligands, more preferably a monovalent ligand and a chelate ligand, especially preferably a chelate ligand which has a plurality of, such as two or three, trivalent phosphorus atoms capable of bonding to the said nickel(0), each of which may be present independently as a phosphine, phosphinite, phosphonite or phosphite. Particularly advantageously, the catalyst should also contain a Lewis acid. Such catalyst systems are known per se.

The present invention is illustrated in detail with reference to the following examples:

WORKING EXAMPLE

Homogeneously Catalyzed Isomerization of cis-2-pentenenitril in a Mixture with trans-3-pentenenitrile The examples 1 and 2 which follow are intended to illustrate the isomerizability with addition of a homogeneously dissolved substance.

Example 1

Procedure:

A three-neck flask is initially charged with 30 g of cis-2-pentenenitrile (gas chromatography analysis in area %: 98.74% cis-pentenenitrile, 0.64% Z-2-methyl-2-butenenitrile, 0.40% trans-2-pentenenitrile, 0.22% 4-pentenenitrile). A defined amount of hexylamine is subsequently added to the cis-2-pentenenitrile. Via one neck, a thermometer is conducted into the flask, to the middle neck is attached a reflux condenser and, at the third neck, the flask is sealed using a septum for sampling during the experiment. Before and during the experiment, the apparatus is flushed with argon. After the sealing, the flask is heated in an oil bath to an internal temperature of 100° C. At regular intervals, samples are taken via the septum using a syringe and analyzed by means of gas chromatography. At the start of the experiment, there is a clear, colorless phase; after the end of the experiment, there is still a clear phase which is now slightly yellow-colored. Hexylamine has no mobility on the Stabilwax column used in the gas chromatograph, which is why the nitriles are responsible for virtually 100% of the GC peaks. All components having higher retention times and trans-3-pentenenitrile are combined under the high boilers component.

In this example, the experiment is carried out with addition of 6.0 g of hexylamine.

Abbreviations Used:
Z2M2BN: Z-2-methyl-2-butenenitrile
C2PN: cis-2-pentenenitrile
T2PN: trans-2-pentenenitrile
4PN: 4-pentenenitrile
T3PN: trans-3-pentenenitrile.

Results

| Run time | Z2M2BN | C2PN | T2PN | 4PN | T3PN | High boilers |
|---|---|---|---|---|---|---|
| 0 h | 0.64% | 98.74% | 0.40% | 0.22% | 0.00% | 0.00% |
| 2 h | 0.64% | 93.01% | 1.02% | 4.14% | 0.82% | 0.37% |
| 4 h | 0.64% | 88.09% | 2.03% | 7.36% | 1.18% | 0.71% |
| 6 h | 0.64% | 83.65% | 3.24% | 10.09% | 1.36% | 1.02% |

Example 2

Procedure:
As described in example 1.
In this example, the experiment is carried out with addition of 15.0 g of hexylamine.

Results

| Run time | Z2M2BN | C2PN | T2PN | 4PN | T3PN | High boilers |
|---|---|---|---|---|---|---|
| 0 h | 0.63% | 98.10% | 0.46% | 0.53% | 0.00% | 0.00% |
| 2 h | 0.62% | 80.63% | 4.15% | 11.42% | 1.30% | 1.58% |
| 4 h | 0.61% | 70.42% | 7.88% | 16.45% | 1.53% | 3.13% |
| 6 h | 0.61% | 62.77% | 11.51% | 18.97% | 1.60% | 4.53% |

Examples 1 and 2 show that, owing to the addition of hexylamine, the formation of isomers of cis-2-pentenenitrile takes place. Hexylamine is dissolved homogeneously.

What is claimed is:

1. A process for isomerizing cis-2-pentenenitrile to trans-3-pentenenitrile comprising contacting a reactant stream comprising the cis-2-pentenenitrile with at least one homogeneous catalyst, wherein the catalyst is a $C_1$- to $C_{20}$-monoamine or a $C_1$- to $C_{20}$-diamine, or an ionic liquid, the ionic liquid being selected from the group consisting of Brønsted acid adducts of organic nitrogen-containing substances.

2. The process according to claim 1, wherein the isomerization is conducted in at least one reactor and includes at least one distillation apparatus, the reactors, if more than one reactor is used, being connected directly in series, and the distillation apparatuses, if more than one distillation apparatus is used, being connected directly in series, and the at least one distillation apparatus being connected downstream of the at least one reactor.

3. The process according to claim 1, which is carried out in more than one apparatus connection, the individual apparatus connections being connected in series and the individual apparatus connections comprising at least one reactor and at least one distillation apparatus, the reactors of the individual apparatus connections, if more than one reactor is used in the apparatus connection, being connected directly in series, and the distillation apparatuses of the individual apparatus connections, if more than one distillation apparatus is used in the particular apparatus connection, being connected directly in series, and the at least one distillation apparatus being connected downstream of the at least one reactor in the particular apparatus connection.

4. The process according to claim 1, wherein the isomerization is carried out in a distillation column.

5. The process according to claim 1, wherein the reactant stream further comprises components selected from a group consisting of C5-mononitriles, C6-dinitriles, aliphatic C1- to C16-alkanes, cyclic C1- to C16-alkanes, aliphatic C1- to C16-alkenes, and cyclic C1- to C16-alkenes.

6. The process according to claim 1, wherein the reactant stream is generated by the hydrocyanation of 3-pentenenitrile.

7. The process according to claim 1, wherein at least one catalyst is a $C_4$-$C_9$ diamine, or hexylamine.

8. The process according to claim 6, wherein at least one catalyst is a $C_4$-$C_9$ diamine, or hexylamine.

* * * * *